United States Patent
Lucast et al.

(10) Patent No.: US 6,479,073 B1
(45) Date of Patent: *Nov. 12, 2002

(54) PRESSURE SENSITIVE ADHESIVE ARTICLES AND METHODS FOR PREPARING SAME

(75) Inventors: Donald H. Lucast, North St. Paul, MN (US); Richard J. Goetz, Woodbury, MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/726,513

(22) Filed: Oct. 7, 1996

(51) Int. Cl.[7] .............................. A61K 9/70; A61L 15/58
(52) U.S. Cl. ........................ 424/448; 424/484; 424/443; 428/327
(58) Field of Search .................. 424/486, 484, 424/448, 489, 443, 497; 428/283, 327, 343

(56) References Cited

U.S. PATENT DOCUMENTS

| | | | |
|---|---|---|---|
| RE24,906 E | | 12/1960 | Ulrich .......................... 206/59 |
| 2,976,576 A | * | 3/1961 | Wichterle et al. |
| 3,220,960 A | * | 11/1965 | Wichterle et al. |
| 3,598,123 A | * | 8/1971 | Zaffaroni |
| 3,731,683 A | * | 5/1973 | Zaffaroni |
| 3,734,097 A | | 5/1973 | Zaffaroni ................... 128/268 |
| 3,857,731 A | | 12/1974 | Merrill, Jr. et al. .......... 117/122 |
| 3,996,934 A | * | 12/1976 | Zaffaroni ................... 424/449 |
| 4,049,483 A | | 9/1977 | Loder et al. ................. 156/230 |
| 4,170,612 A | * | 10/1979 | Pastor et al. |
| 4,216,134 A | * | 8/1980 | Brenner |
| 4,231,369 A | | 11/1980 | Sorensen et al. ........... 128/283 |
| 4,310,509 A | * | 1/1982 | Berglund et al. |
| 4,624,893 A | | 11/1986 | Shibano et al. ............. 428/327 |
| 4,636,432 A | | 1/1987 | Shibano et al. ............. 428/327 |
| 4,693,776 A | | 9/1987 | Krampe et al. ............. 156/327 |
| 4,735,837 A | | 4/1988 | Miyasaka et al. ............. 428/40 |
| 4,855,170 A | | 8/1989 | Darvell et al. ................. 428/40 |
| 4,952,618 A | | 8/1990 | Olsen .......................... 524/17 |
| 4,994,322 A | | 2/1991 | Delgado et al. ............. 428/343 |
| 5,052,381 A | * | 10/1991 | Gilbert et al. |
| 5,118,750 A | | 6/1992 | Silver et al. ................. 524/462 |
| 5,196,246 A | | 3/1993 | Kauss et al. .................. 428/39 |
| 5,266,402 A | | 11/1993 | Delgado et al. ............. 428/355 |
| 5,270,358 A | | 12/1993 | Asmus ......................... 524/55 |
| 5,296,277 A | | 3/1994 | Wilson et al. ................. 428/40 |
| 5,369,155 A | | 11/1994 | Asmus ......................... 524/55 |
| 5,378,405 A | * | 1/1995 | Gutman et al. ............. 524/801 |
| 5,407,717 A | * | 4/1995 | Lucast et al. ............... 526/264 |
| 5,484,600 A | * | 1/1996 | Sjogren |
| 5,486,158 A | | 1/1996 | Samuelsen ................... 602/46 |
| 5,508,313 A | * | 4/1996 | Delgado et al. ............. 524/548 |
| 5,514,122 A | | 5/1996 | Morris et al. |
| 5,549,908 A | * | 8/1996 | Smith et al. ................. 424/444 |
| 5,595,821 A | * | 1/1997 | Hager et al. ................. 526/286 |

FOREIGN PATENT DOCUMENTS

| | | |
|---|---|---|
| EP | 0 591 898 A1 | 4/1984 |
| EP | 0 272 149 A2 | 6/1988 |
| EP | 0 554 832 A1 | 8/1993 |
| EP | 0 658 351 A1 | 6/1995 |
| WO | PCT/US92/00613 | 1/1992 |
| WO | PCT/US92/06570 | 8/1992 |
| WO | PCT/US92/10588 | 12/1992 |
| WO | PCT/US94/03180 | 3/1994 |
| WO | PCT/US95/02314 | 2/1995 |
| WO | PCT/US95/12193 | 9/1995 |
| WO | WO 95/31225 | 11/1995 |
| WO | WO 96/14094 | 5/1996 |

OTHER PUBLICATIONS

The Merck Index, 11Ed, 1989, p. 685.*

* cited by examiner

*Primary Examiner*—Edward J. Webman
(74) *Attorney, Agent, or Firm*—John A. Burtis

(57) ABSTRACT

An article that includes a substrate having a surface, at least a portion of which is provided with a pressure sensitive adhesive composition that includes a blend of discrete, crosslinked polymer microspheres and a polymer matrix. The composition has a substantially smooth, exposed surface available for adhesion.

9 Claims, No Drawings

US 6,479,073 B1

PRESSURE SENSITIVE ADHESIVE ARTICLES AND METHODS FOR PREPARING SAME

BACKGROUND OF THE INVENTION

The invention relates to adhering a substrate to a surface such as skin using a pressure sensitive adhesive.

Pressure Sensitive Adhesives (PSAs) are normally tacky at room temperature and typically can form a bond to a surface by, at most, light finger pressure. Pressure sensitive adhesive tapes have been used for a variety of marking, holding, protecting, sealing and masking purposes. PSA tapes have many uses in medical applications as well. Such applications typically involve adhering the tape to skin. The irregular and complex surface of the skin presents obstacles in itself, and the wide variation in the skin surface from individual to individual and from one position on the individual to another position compounds these obstacles.

SUMMARY OF THE INVENTION

In a first aspect, the invention features an article that includes a substrate having a surface, at least a portion of which is provided with a pressure sensitive adhesive composition that includes a blend of discrete, crosslinked polymer microspheres and a polymer matrix. The adhesive composition has a substantially smooth, exposed surface available for adhesion.

The microspheres can be tacky microspheres, solid microspheres, hollow microspheres, tack-free microspheres or plastic microspheres. Preferred microspheres comprise tacky, hollow microspheres. In a preferred embodiment, the adhesive composition includes between about 1% and about 75% percent by volume of the microspheres.

The microspheres preferably have an average diameter between about 1 micrometer and about 300 micrometers. A preferred matrix polymer includes an acrylic polymer.

In a preferred embodiment, the thickness of the adhesive composition on the substrate is between about 10 micrometers and about 300 micrometers. The article is preferably substantially transparent upon observation by the naked eye. For example, the article is sufficiently transparent such that a health care worker can observe the skin underlying the article.

The adhesive composition can be in the form of a substantially continuous coating on the surface of the substrate or a discontinuous coating on the surface of the substrate. The microspheres preferably include the reaction product of iso-octylacrylate, acrylic acid, and poly(ethylene oxide) acrylate.

In another aspect, the invention features an article adapted for adhesion to the skin of a patient that includes a substrate having a surface, at least a portion of which is provided with a pressure sensitive adhesive composition that includes a blend of discrete, crosslinked polymer microspheres and a polymer matrix. The adhesive composition has a substantially smooth, exposed surface available for adhesion. The article may be provided, e.g., in the form of a skin patch, wound dressing, adhesive bandage, or island dressing.

In a third aspect, the invention features a method of making an article including the steps of:
(a) preparing a pressure sensitive adhesive composition including a blend of discrete, crosslinked polymer microspheres and a polymer matrix; and
(b) depositing the blend on at least a portion of a substrate in the form of a coating, the average microsphere diameter, the volume fraction of the microspheres in the composition and the thickness of the coating being selected such that the coating has a substantially smooth, exposed surface available for adhesion.

The smooth surface of the adhesives of the present invention provides for more extensive contact with an opposing surface than corresponding adhesives with protruding microspheres. As a result, the initial peel adhesion of the adhesive composition generally is relatively high. Also, the adhesive composition does not exhibit unacceptably high adhesion build-up over time when adhered to an opposing surface. The refractive indices of the polymer microspheres and matrix are generally substantially the same, making it possible to prepare a substantially transparent article. Such articles, in turn, permit observation of the substrate to which the article is adhered. This feature is particularly useful in medical applications because it enables examination of the underlying skin.

Other advantages and features of the invention will be apparent from the detailed description and from the claims.

DESCRIPTION OF THE PREFERRED EMBODIMENTS

The invention is directed to articles featuring a substrate coated with a pressure sensitive adhesive composition that includes a polymer matrix blended with discrete, crosslinked polymer microspheres. The average microsphere diameter, volume fraction of microspheres and coating thickness are selected such that when the adhesive composition is applied to the substrate, the adhesive composition forms an exposed surface available for adhesion that is substantially smooth on a scale on the order of the size of the microspheres.

Smoothness of the exposed surface on this order indicates that the microspheres are not protruding from the plane of the surface. This is in contrast to adhesives where protrusion of polymer microspheres, whether or not covered by polymer matrix, provides for positionability. Positionability of adhesives with protruding microspheres is due, at least partly, to more limited point contact with the protruding regions during adhesion to an opposing surface.

The substrate generally can be made from any material suitable for the particular application envisioned for the article. Preferred substrates exhibit a desired combination of properties such as moisture vapor permeability, texture, conformability, yield modulus, appearance, processability, and strength. A substrate can have structure on its surface as long as the structure does not interfere with the formation of a smooth layer of adhesive at an appropriate adhesive thickness. For certain applications (e.g., transparent dressings), it is preferred for the substrates to be substantially transparent upon observation by the naked eye of an observer.

Suitable materials for flexible substrates include paper, latex saturated paper, polymeric film, metallic foil, and ceramic sheeting. Appropriate materials for polymeric films include cellulose acetate film, ethyl cellulose film, polyolefins (such as polyethylene and polypropylene, including isotactic polypropylene), polystyrene, polyvinyl alcohol, polyester (e.g., poly(ethylene terephthalate) or poly (butylene terephthalate)), poly(caprolactam), poly (vinylidene fluoride), and the like. Suitable substrates also include commercially available fabrics such as non-woven, woven or knitted fabrics. Such fabrics may be constructed from a wide range of synthetic or natural fibers, used singly or in blends. Examples of suitable non-woven fabrics include carded, spun-bonded, spun-laced, air-laid, blown microfibrous constructions, and stitch-bonded fabrics.

Suitable commercially available substrate materials include kraft paper (available from Monadnock Paper, Inc.); cellophane (available from Flexel Corp.); spun-bond poly (ethylene) and polypropylene, such as Tyvek™ and Typar™ (available from DuPont, Inc.); and porous films obtained from polyethylene and poly(propylene), such as Teslin™ (available from PPG Industries, Inc.), and Cellguard™ (available from Hoechst-Celanese).

Release coated substrates can also be used. Such substrates are typically employed when an adhesive transfer tape is provided. Examples of release coated substrates include silicone coated kraft paper and the like. Tapes of the invention may also incorporate a low adhesion backsize (LAB). The LAB typically is applied to the substrate surface that is opposite the surface bearing the pressure sensitive adhesive.

The adhesive compositions of the present invention are particularly suitable for the production of medical articles intended for adhesion to skin. Examples include tapes, skin patches, strips, wound dressings, monitoring or neurostimulating electrodes, transparent adhesive dressings, island dressings (with absorbent polymeric or fabric islands), consumer first aid dressings, drapes, and the like. Suitable substrates for these applications include conformable backing materials that are known in the medical or surgical fields. Useful substrates include nonwoven fabrics, woven fabrics, knit fabrics, and low to medium tensile modulus synthetic films such as polypropylene, polyethylene, polyvinyl chloride, polyurethane, low modulus polyester and ethyl cellulose. Fabrics can be made from materials such as cotton, nylon, rayon or other natural or synthetic fibers or blends. The films preferably have a tensile modulus less than about 400,000 psi as measured in accordance with ASTM D-638 and D-882 procedures, preferably less than about 300,000 psi.

The desirable features of the adhesives for these applications include relatively high initial peel adhesion, minimal adhesion build-up over time and, optionally, transparency. Preferred articles have moisture vapor transmission rates, when tested in accordance with ASTM E-96-80, of at least about 500 g/m$^2$, over 24 hours at 38° C., with a humidity differential of 80 percent, more preferably 1000 g/m$^2$.

In addition, it has been found that the higher the creep compliance, the greater the quantity of adhesive residue left on the skin after removal of the adhesive coated article. Creep compliance is a rheological property relating to the flow of the adhesive. Accordingly, creep compliance values less than $2.3 \times 10^{-5}$ cm$^2$/dyne are preferred. Measurement of creep compliance values is described below.

Preferred substrates have a high rate of moisture vapor transmission. For example, a continuous film substrate of 25 μm thickness prepared from a polyurethane sold under the tradename Estane 58309, available from B. F. Goodrich, and a continuous film substrate prepared from a polyester sold under the tradename Hytrel 4053, available from DuPont, each have moisture vapor transmission values of about 1000 to about 1500 g/m$^2$/24 hours. Woven substrates such as those used for DURAPORE™ tape, available from 3M, have even higher values.

The adhesive compositions will now be described in greater detail. All amounts are in weight percent unless otherwise noted.

Polymer Matrix

The polymer matrix preferably is a pressure sensitive adhesive. It can be formed from a variety of materials. Suitable materials for the matrix include rubber resin polymers, including natural or synthetic rubber and block copolymers, and free radically polymerizable acrylic pressure sensitive adhesive compositions. The acrylic adhesives are less prone to discoloration and are amenable to precise control during preparation.

The acrylate monomers are typically alkyl acrylates, preferably monofunctional unsaturated acrylate esters of non-tertiary alkyl alcohols, the alkyl groups of which have from 2 to about 14 carbon atoms, providing a polymer having a glass transition temperature (Tg) of less than 0° C., preferably less than –10° C. Included within this class of preferred monomers are, for example, iso-octyl acrylate, iso-nonyl acrylate, 2-ethyl-hexyl acrylate, decyl acrylate, dodecyl acrylate, n-butyl acrylate, hexyl acrylate, and mixtures thereof.

The alkyl acrylate monomers can be used to form homopolymers, or they can be copolymerized with polar copolymerizable monomers or higher Tg monomers (higher than the alkyl acrylate) such as some vinyl esters, and $C_1$ to $C_4$ alkyl esters of (meth)acrylic acid and/or styrene. When copolymerized with polar monomers, the alkyl acrylate monomer generally comprises at least about 70% of the polymerizable monomer composition. A portion of high Tg monomers can be used as long as the Tg of the resulting copolymer is less than about 10° C.

The polar copolymerizable monomers can be selected from monomers such as monoolefinic mono- and dicarboxylic acids, hydroxyalkyl acrylates, cyanoalkyl acrylates, acrylamides or substituted acrylamides, N-vinyl pyrrolidone, acrylonitrile, vinyl chloride and diallyl phthalate. The polar monomer preferably comprises up to about 25%, more preferably up to about 15%, of the polymerizable monomer composition.

Optionally, a low molecular weight hydrophobic polymer can be added to the adhesive matrix monomers to improve emulsion stability. These polymers preferably have an average molecular weight from 400 to 50,000 and include polystyrene resins, poly(methylmethacrylate) resin, polybutadiene, polyisoprene, poly(alphamethylstyrene), polydiene-polyaromatic arene copolymers, rosin esters and mixtures thereof. These may be added in amounts up to 20% of the monomer mixture, preferably up to 10%.

Also usable are copolymerizable ionic surfactants to improve cohesive strength and moisture resistance. These include polyalkylene polyalkoxy ammonium sulfate (e.g., "MAZON" SAM-211 available from PPG Industries) and alkyl allyl sulfosuccinates (e.g., "TREM" LF40 available from Diamond Shamrock Co.) as well as those described in PCT application No. WO 89/12618 and U.S. Pat. Nos. 3,925,442 and 3,983,166. Non-copolymerizable ionic and nonionic surfactants can be used instead of the copolymerizable surfactants but are less preferred. The surfactants can be used in amounts of from 0 to 10% of the total monomer component, preferably 1.5 to 5%.

The pressure sensitive adhesive matrix is prepared from a polymerizable composition preferably containing initiator to aid in polymerization of the monomers. Suitable initiators include thermally-activated initiators where the initiator is water or oil soluble. Suitable oil soluble initiators include azo and diazo compounds, hydroperoxides, peroxides, and the like. Water soluble initiators include persulfates such as potassium persulfate. Generally, the initiator is present in an amount from about 0.01% to about 3.0%, preferably 0.1 to 0.5%, based on the total monomer component.

Where superior cohesive strengths are desired, the pressure sensitive adhesive matrix may also be cross-linked.

Preferred crosslinking agents for the acrylic pressure-sensitive adhesive matrix are multiacrylates such as 1,6-hexanediol diacrylate, as well as those disclosed in U.S. Pat. No. 4,379,201 (Heilmann et al.), incorporated herein by reference. Photo-initiators can act as post-cure crosslinkers. Examples include the benzoin ethers, substituted benzoin ethers such as benzoin methyl ether or benzoin iso-propyl ether, substituted acetophenones such as 2,2-diethoxy-acetophenone, and 2,2-dimethoxy-2-phenyl-acetophenone, substituted alpha-ketols such as 2-methyl-2-hydroxypropiophenone, aromatic sulphonyl chlorides such as 2-naphthalene sulphonyl chloride, and photoactive oximes such as 1-phenyl-1,1-propanedione-2-(O-ethoxycarbonyl)oxime. Each of the crosslinking agents is useful in the range of from about 0.01% to about 3%, preferably 0.1 to 1%, of the total components.

Other useful materials that can be blended into the adhesive matrix include, but are not limited to, fillers, pigments, plasticizers, tackifiers, fibrous reinforcing agents, woven and nonwoven fabrics, foaming agents, antioxidants, stabilizers, fire retardants, and rheological modifiers. Chain transfer agents, such as carbon tetrabromide, mercaptans or alcohols, can be used in the monomer mixture to adjust the molecular weight of the resulting polymer.

Microspheres

The polymer microspheres are crosslinked. In addition, they can be solid or hollow and tacky or tack-free. Tack-free microspheres can be elastomeric or plastic. The specific type of microsphere can be selected to yield the desired properties of the adhesive composition for the particular application. The microspheres should be water and solvent insoluble, but solvent dispersible. Furthermore, the microspheres may be swellable in organic solvents. Polymer microspheres preferably are formed by free radical suspension polymerization.

The diameter of the individual microspheres preferably is selected such that the adhesive forms a smooth surface for a given microsphere volume fraction and coating thickness. The microspheres generally will have an average diameter between about 1 micrometer ($\mu$m) and 300 $\mu$m, more preferably between 5 $\mu$m and 100 $\mu$m and even more preferably between 10 $\mu$m and 70 $\mu$m. When the microspheres are hollow, the voids typically range in size from less than 1 $\mu$m up to about 100 $\mu$m or larger.

For the formation of tacky or tack-free, elastomeric microspheres, preferred monomers include vinyl esters, acrylates and methacrylates, alone or in combination with each other such that the Tg of the polymer is less than about room temperature. Combinations of monomers that result in a Tg greater than room temperature will result in plastic, tack-free microspheres. Examples of appropriate monomers for the formation of elastomeric microspheres include iso-octyl acrylate, iso-nonyl acryiate, iso-amyl acrylate, 2-ethylhexyl acrylate, n-butyl acrylate, sec-butyl acrylate, tert-butyl acrylate, iso-bornyl acrylate, butyl methacrylate, vinyl acetate, acrylonitrile, iso-decyl acrylate, iso-decyl methacrylate, 2-methylbutyl acrylate, 4-methyl-2-pentyl acrylate, and ethyl acrylate.

Examples of suitable vinyl ester monomers include vinyl 2-ethylhexanoate, vinyl caprate, vinyl laurate, vinyl pelargonate, vinyl hexanoate, vinyl propionate, vinyl decanoate, vinyl octanoate, and other monofunctional unsaturated vinyl esters of linear or branched carboxylic acids comprising 1 to 14 carbon atoms. Preferred vinyl ester monomers include vinyl laurate, vinyl caprate, vinyl-2-ethylhexanoate, and mixtures thereof.

The vinyl esters, acrylates or methacrylates may be copolymerized with other vinyl monomers including styrene, substituted styrenes, vinyl benzene, N-iso-octylacrylamide, vinyl chloride and vinylidene chloride. Minor amounts of other comonomers known in the art can be employed, provided that the Tg of the resulting copolymer stays within the desired range.

For the formation of plastic microspheres, free radically polymerizable monomers are selected that are capable of forming homo- or co-polymers having glass transition temperatures generally above 20° C. Suitable monomers or comonomers include vinyl esters, alkyl acrylates, alkyl methacrylates, styrenes and substituted styrenes, cyclic alkyl acrylates and methacrylates, aryl acrylates and methacrylates and mixtures thereof. Suitable vinyl esters include vinyl neonanoate, vinyl pivalic acid ester, vinyl acetate, vinyl propionate, and vinyl neodecanoate. Acrylates and methacrylates can be used provided that they do not cause the resultant polymer to have a Tg or Tm of less than about 10° C. For plastic microspheres, preferred are acrylates and methacrylates which will produce homopolymers or copolymers having Tg higher than about 0° C. and preferably higher than about 10° C. Suitable acrylates and methacrylates include tert-butyl acrylate, iso-bornyl acrylate, butyl methacrylate, vinyl acetate, acrylonitrile, iso-nonal acrylate, iso-decyl acrylate, iso-decyl methacrylate, sec-butyl acrylate, iso-amyl acrylate, 2-methylbutyl acrylate, 4-methyl-2-pentyl acrylate, iso-decyl acrylate, ethyl acrylate and mixtures thereof. Suitable acrylates can be copolymerized with vinyl esters and other suitable comonomers.

Also useful as comonomers are other vinyl monomers such as vinyl benzene, divinyl benzene, N-iso-octylacrylamide, which can be used in conjunction with the vinyl ester, acrylate, methacrylate or acrylic monomers. Minor amounts of other comonomers known in the art can be employed, provided that the Tg of the comonomer stays within the desired range.

For the production of either elastomeric or plastic microspheres, other suitable co-monomers include polar co-monomers, e.g., monoolefinic monocarboxylic acids, monoolefinic dicarboxylic acids, acrylamides, N-substituted acrylamides, salts thereof, and mixtures thereof. Specific examples include acrylic acid, methacrylic acid, itaconic acid, crotonic acid, maleic acid, fumaric acid, sulfoethyl methacrylate, and ionic monomers such as sodium methacrylate, ammonium acrylate, sodium acrylate, trimethylamine p-vinyl benzimide, 4,4,9-trimethyl-4-azonia-7-oxo-8-oxa-dec-9-ene-1-sulphonate, N,N-dimethyl-N-(beta-methacryloxy-ethyl) ammonium propionate betaine, trimethylamine methacrylimide, 1,1-dimethyl-l-(2,3-dihydroxypropyl)amine methacrylimide, N-vinyl pyrrolidone, N-vinyl caprolactam, acrylamide, t-butyl acrylamide, dimethyl amino ethyl acrylamide, N-octyl acrylamide, mixtures thereof, and the like. Preferred polar monomers include monoolefinic monocarboxylic acids, monoolefinic dicarboxylic acids, acrylamides, N-substituted acrylamides, salts thereof and mixtures thereof. Examples of such monomers include but are not limited to acrylic acid, sodium acrylate, N-vinyl pyrrolidone, and mixtures thereof.

Hydrophilizing agents or components can also be used as co-monomers to produce microspheres with pendent hydrophilic moieties. The hydrophilizing agents can act as crosslinkers when they are multi-functional. Preferred are free radically reactive hydrophilic oligomers (a polymer having a low number of repeating units, generally 2 to 20) and/or polymers including poly(alkylene oxides) (e.g., poly(ethylene oxide)), poly(vinyl methyl ether), poly(acrylamide), poly(N-vinylpyrrolidone), poly(vinyl alcohol), cellulose derivatives and mixtures thereof.

Other suitable hydrophilizing co-monomers include macromonomers, e.g., acrylate terminated poly(ethylene oxide), methacrylate terminated poly(ethylene oxide), methoxy poly(ethylene oxide) methacrylate, butoxy poly(ethylene oxide) methacrylate, p-vinyl benzyl terminated poly(ethylene oxide), acrylate terminated poly(ethylene glycol), methacrylate terminated poly(ethylene glycol), methoxy poly(ethylene glycol) methacrylate, butoxy poly(ethylene glycol) methacrylate, p-vinyl benzyl terminated poly(ethylene glycol), poly(ethylene oxide) diacrylate, poly(ethylene oxide) dimethacrylate, and mixtures thereof. These functionalized materials are preferred because they are easily prepared through well-known ionic polymerization techniques and are also highly effective in providing grafted hydrophilic segments along free radically polymerized microsphere polymer backbones.

Other examples of suitable macromonomers include p-vinyl benzyl terminated poly(N-vinyl pyrrolidone), p-vinyl benzyl terminated poly(acrylamide), methacrylate terminated poly(N-vinyl pyrrolidone), and mixtures thereof. These macromonomers may be prepared through the esterification reaction of a carboxy terminated N-vinyl pyrrolidone or acrylamide, beta-mercaptopropionic acid chain transfer agent, and chloromethyl styrene or methacryloyl chloride as described in a series of papers by M. Acacia et al. [*Angew, Makromol, Chem.*, 132, 81 (1985); *J. Appl. Polym. Sci.*, 39, 2027 (1990); *J. Polym. Sci.*, Part A: *Polym. Chem.*, 27, 3521 (1989)].

The elastomeric microspheres preferably comprise at least about 70 parts of at least one free radically polymerizable monomer, optionally up to about 30 parts of one or more polar monomers, and about 0 to about 30 parts of at least one hydrophilizing component.

More preferably, the elastomeric microspheres comprise about 80 to about 100 parts, most preferably 90 to 100 parts, of one or more free radically polymerizable monomers selected from the group consisting of alkyl acrylate esters, alkyl methacrylate esters, vinyl esters, and mixtures thereof where the alkyl group is a $C_4$ to $C_{12}$ alkyl, optionally up to about 10 parts of at least one polar monomer, and optionally up to about 10 parts of a hydrophilizing component. Most preferably the microspheres comprise about 95 to about 99.9 parts of the free radically polymerizable monomers, up to about 5.0 parts of a hydrophilizing component, and, optionally, about 0.1 to about 5.0 parts of a polar monomer.

The composition from which the elastomeric or plastic microspheres of the invention are made may also contain a multifunctional crosslinking agent. The term "multifunctional" as used herein refers to crosslinking agents which possess two or more free radically polymerizable ethylenically unsaturated groups. Useful multifunctional crosslinking agents include acrylic or methacrylic esters of diols such as butanediol diacrylate, triols such as glycerol, and tetraols such as pentaerythritol. Other useful crosslinking agents include polymeric multifunctional (meth)acrylates, e.g., poly(ethylene oxide) diacrylate or poly(ethylene) oxide dimethacrylate; polyvinylic crosslinking agents, such as substituted and unsubstituted divinylbenzene; and difunctional urethane acrylates, such as "EBECRYL" 270 and "EBECRYL" 230 (1500 weight average molecular weight and 5000 weight average molecular weight acrylated urethanes, respectively—both available from Radcure Specialties), and mixtures thereof.

When a crosslinker is employed, it is typically employed at a level of up to about 10 equivalent weight percent. Above about 0.15 equivalent weight percent, based on the total polymerizable microsphere composition, most elastomeric microspheres become tack-free. The "equivalent weight percent" of a given compound is defined as the number of equivalents of that compound divided by the total number of equivalents in the total (microsphere) composition, where an equivalent is the number of grams divided by the equivalent weight. The equivalent weight is defined as the molecular weight divided by the number of polymerizable groups in the monomer (in the case of those monomers with only one polymerizable group, equivalent weight=molecular weight). The crosslinker can be added at any time before 100% conversion to polymer of the monomers of the microsphere composition. Preferably, crosslinker is added before initiation occurs.

The relative amounts of the components are important to the properties of the resultant microspheres. Generally, the greater the amount of crosslinker the less tack in the resulting microspheres. Tacky microspheres generally include crosslinkers up to concentrations where the crosslinkers contribute about 0.15% of the total polymerizable functional groups.

The plastic microspheres preferably comprise at least about 80 parts of at least one free radically polymerizable monomer, optionally up to about 5 parts of one or more polar monomers, about 0 to about 15 parts of at least one hydrophilizing component crosslinked with at least one multifunctional crosslinker. An additional initiator and/or other multifunctional crosslinker and other additives may also be used. More preferably, the microspheres include about 95 to about 100 parts of free radically polymerizable monomer selected from the group consisting of alkyl acrylate esters, alkyl methacrylate esters, vinyl esters, and mixtures thereof, optionally about 0 to about 3 parts of at least one polar monomer, and optionally about 0 to about 2 parts of a hydrophilizing component.

If hollow, elastomeric or plastic microspheres are desired, they may be obtained via a "two-step" process comprising the steps of:
(a) forming a water-in-oil emulsion by mixing (1) an aqueous solution (which may contain some of the carbonyl monomer and/or some of the optional polar monomer) with (2) oil phase base monomers, a free radical polymerization initiator, and internal crosslinking agent (if any is used);
(b) forming a water-in-oil-in-water emulsion by dispersing the water-in-oil emulsion from step
(a) into an aqueous phase (containing any of the carbonyl monomer and/or polar monomer not added in step (a)); and
(c) initiating suspension polymerization, usually by applying heat (preferably about 40 to 60° C., more preferably about 50 to 60° C.) or radiation (e.g., ultraviolet radiation).

Emulsifiers having a low hydrophilic-lipophilic balance (HLB) value are used to facilitate the formation (usually by agitation) of the water-in-oil emulsion in the first step. Suitable emulsifiers are those having an HLB value below about 7, preferably in the range of about 2 to 7. Examples of such emulsifiers include sorbitan monooleate, sorbitan trioleate, and ethoxylated oleyl alcohol such as Brij™ 93, available from Atlas Chemical Industries, Inc. A thickening agent, e.g., methyl cellulose, may also be included in the aqueous phase of the water-in-oil emulsion.

The aqueous phase into which the water-in-oil emulsion is dispersed in step (b) contains an emulsifier having an HLB value above about 7. Examples of such emulsifiers include ethoxylated sorbitan monooleate, ethoxylated lauryl alcohol, and alkyl sulfates. The emulsifier concentration (for both steps (a) and (b)) should be greater than its critical micelle concentration, which refers to the minimum concentration of emulsifier necessary for the formation of micelles, i.e., submicroscopic aggregations of emulsifier molecules. Critical micelle concentration is slightly different for each emulsifier, usable concentrations ranging from about $1.0 \times 10^{-4}$ to about 3.0 moles/liter. Additional detail concerning the preparation of water-in-oil-in-water emulsions, i.e. multiple emulsions, may be found in various literature references, e.g., Surfactant Systems: Their Chemistry, Pharmacy, & Biology, (D. Attwood and A. T. Florence, Chapman & Hall Limited, New York, 1983).

Useful initiators are those which are normally suitable for free radical polymerization of acrylate or vinyl ester monomers and which are oil soluble and of very low solubility in water, typically less than 1 g/100 g water at 20° C. Examples of such initiators include azo compounds, hydroperoxides, peroxides, and the like, and photoinitiators such as benzophenone, benzoin ethyl ether, 2,2-dimethoxy-2-phenyl acetophenone. The initiator is generally used in an amount ranging from about 0.01% up to about 10% by weight of the total polymerizable composition, preferably up to about Use of a substantially water soluble polymerization initiator, such as those generally used in emulsion polymerizations, causes formation of substantial amounts of latex. During suspension polymerization, any significant formation of latex is undesirable because of the extremely small particle size.

Hollow microspheres may also be prepared by a simpler "one-step" process comprising aqueous suspension polymerization of the carbonyl monomer, the base monomer, and the polar monomer (which is not optional for this process) in the presence of an emulsifier which is capable of producing, inside the droplets, a water-in-oil emulsion that is substantially stable during both formation of the emulsion and subsequent suspension polymerization.

Useful emulsifiers are anionic materials having an HLB value greater than 25 and include alkylaryl ether sulfates such as sodium alkylaryl ether sulfate, e.g., Triton™ W/30, available from Rohm and Haas; alkylaryl poly(ether) sulfates such as alkylaryl poly(ethylene oxide) sulfates, preferably those having up to about 4 ethoxy repeat units; and alkyl sulfates, such as sodium lauryl sulfate, and sodium hexadecyl sulfate, triethanolamine lauryl sulfate, and sodium hexadecyl sulfate; alkyl poly(ether) sulfates, such as alkyl poly(ethylene oxide) sulfates, preferably those having up to about 4 ethoxy units. Alkyl sulfates, alkyl ether sulfates, alkylaryl ether sulfates, and mixtures thereof are preferred.

Non-ionic emulsifiers having an HLB value of between about 13 and 25 can be utilized in conjunction with the anionic emulsifiers. Examples of non-ionic emulsifiers include Siponic™ Y-500-70 (ethoxylated oleyl alcohol, available from Alcolac, Inc.), PLURONIC® P103, and Tween™—40 (from ICI America). As in the two-step process, the emulsifier is utilized in a concentration greater than its critical micelle concentration. Polymeric stabilizers may also be present but are not necessary.

The above-described one-step method may be varied by combining the base monomer with non-ionic emulsifiers, oil soluble polymerization initiator, and any multifunctional internal crosslinker before the base monomer is added to the aqueous phase containing a carbonyl monomer, emulsifier and any optional polar monomer. (The polar monomer is optional for this process.) The resulting emulsion is suspension polymerized to yield hollow pressure sensitive adhesive microspheres. Anionic emulsifiers with an HLB value greater than 7 may be included in the aqueous phase to stabilize the system during suspension polymerization but are not required.

Solid pressure sensitive adhesive microspheres may be prepared via the suspension polymerizations disclosed in U.S. Pat. Nos. 3,691,140; 4,166,152. In general, these suspension polymerization techniques use ionic or non-ionic emulsifiers in an amount greater than the critical micelle concentration and/or protective colloids, finely divided inorganic solids, or the like.

Each suspension polymerization method (whether producing hollow or solid microspheres) may be modified by withholding the addition of all or some of the carbonyl monomer and/or any optional polar monomer until after polymerization of the oil phase base monomer has been initiated. In this instance, however, these components must be added to the polymerizing mixture prior to 100% conversion of the base monomer. Similarly, the internal crosslinker (if used) can be added at any time before 100% conversion to polymer of the monomers of the microsphere composition. Preferably it is added before initiation occurs. The hydrophilizing component can be added to the oil or water phase in the first step or the water phase in the second step, either before or after polymerization is initiated, or some combination of these options.

Following polymerization, an aqueous suspension of the hollow or solid microspheres is obtained which is stable to agglomeration or coagulation under room temperature conditions (i.e., about 20 to about 25° C.). The suspension may have a non-volatile solids content of from about 10 to about 60 percent by weight.

The pressure sensitive adhesive properties of the microspheres may be altered by the addition of tackifying resin and/or plasticizer. Other components, such as pigments, neutralizing agents such as sodium hydroxide, etc., fillers, stabilizers, chain transfer agents, and various polymeric additives may be included as well.

Preparation of the Adhesive Article

The adhesive composition is preferably prepared by blending the polymer matrix with the appropriate quantity of microsphere suspension. The resulting blend is then coated onto a substrate using standard techniques. Alternatively, the blend may be prepared by combining the microspheres with polymerizable monomers and/or oligomers, coating the resulting mixture onto a backing, and then exposing the entire article to an energy source (e.g., heat, ultraviolet radiation, or ionizing radiation) to polymerize the monomers and/or oligomers, thereby forming the polymer matrix. This technique is described generally in Delgado et al., U.S. Pat. No. 5,266,402. The average microsphere diameter, volume fraction of microspheres, and coating thickness are selected such that the adhesive composition forms a substantially smooth surface after being applied to the substrate. The adhesive coating can cover the entire surface of the substrate or only a portion of the surface. Furthermore, the coating can be continuous or discontinuous (e.g., in the form of a dot or grid pattern). For a discussion of discontinuous coatings, see for example U.S. Pat. Nos. 4,595,001 and 4,798,201.

The invention will now be further described by way of the following examples.

EXAMPLES

ABBREVIATIONS

AA=acrylic acid
AmA=Ammonium acrylate
Am90G=poly(ethylene oxide) acrylate, Mw=468
ACM=acrylamide
BDA=Butanediol diacrylate
EOA=poly(ethylene oxide) acrylate, Mw=750
HDDA=1,6-hexanediol diacrylate
IOA=iso-octyl acrylate
Neo9=vinyl-neononanoate, Vynate™ Neo-9 available from Union Carbide of Danbury, Conn.
NVP=N-vinyl pyrrolidone
PSM=polystyrene methacrylate macromonomer, from Polymer Chemistry Innovations of State College, PA
VOAC=vinyl acetate Test Procedures The following tests were used to evaluate the adhesive compositions.

Creep Compliance

To measure creep compliance, a 150-micrometer thickness of the adhesive was coated onto a smooth film of polyester (2 mil thickness). To perform "dry" tests, the coated film then was dried to constant weight by placing it in an air-circulating oven generally for at least 5 minutes at 110° C. The adhesive composition, thus dried, was laminated to itself to form a sandwich, and two test pieces of equal area were die-cut and placed in a parallel plate creep compliance rheometer, one piece being on each side of the center plate, with an outer plate contacting the exposed surface of each. Clamps which connect the two outer plates then were tightened so as to compress the interposed layers of adhesive composition approximately 10%. The parallel plates were placed in horizontal arrangement, and one end of the center plate was connected to a linear variable transducer, which measures the plate displacement (due to adhesive flow). The transducer output, an electrical signal proportional to the displacement, was directed to a chart recorder. A hook was attached to the opposite end of the center plate with a flexible wire extending horizontally from the hook and then downward over a pulley, the outer plates being held in a fixed position. A suitable weight (one sufficient to measurably deform the sample a distance no greater than its thickness) was attached to the free end of the wire, then the strip chart recorder was started. The weight used to exert the stress on the adhesive films weighed 500 grams. From the strip chart recorder, the time and the displacement (strain) are read and the applied force (stress) is recorded. The creep compliance (J) at a given temperature was calculated using the equation:

$$J_{(t)} = 2AX/hf$$

where t is the time at which the measurement is taken, A in cm2 is the area of one face of the adhesive samples, h in cm is the thickness of the adhesive mass, X in cm is the displacement at time t (where X is less than h) and f in dynes is the force due to the mass attached to the wire connected to the middle plate. The compliance value $J_{(t)}$ is given in $cm^2/dyne$. Three measurements were made per sample, and the average value was reported.

To perform "equilibrium" tests rather than "dry" tests, the compliance test is identical to that described above for the dry test except that the coated film is stored for 18–24 hours at a constant temperature of 24° C. and at 50% relative humidity. After storage, the adhesive composition is tested as described above.

Some samples were sterilized with gamma radiation at a dose of 25–45 kilograys (2.5–4.5 Mrads). Gamma treatment was perfomed on selected samples for equilibrium tests and for dry tests.

Creep compliance data for various articles are found in Tables 2–4, 8, 9, 11–14, and 18. The values are reported in $10^{-5}$ $cm^2/dyne$.

Skin Adhesion

The test procedure used is PSTC1, which is Test Method No. 1 of the Pressure-Sensitive Tape Council Brochure, Seventh Edition (1976), Glenview, Ill. The test was modified so that the tape could be applied to the human skin surface on a selected area on the individual's back. Tape samples measuring 2.54 cm wide by 5.08 cm long were placed on the back of an individual and rolled down with one forward and one reverse pass of a 1 kg roller (described in Appendix B, Sections 2.7.1, 2.8.1 and 2.8.2 of the above-referenced brochure) moved at a rate of 30 cm per minute. Adhesion to the skin was measured at a 180 degree peel angle according to PSTC-1 using a strain gauge mounted on a motor-driven carriage. The force of removal is reported in grams of adhesion per 2.54 cm of sample. The rate of removal was 15 cm per minute. Initial skin adhesion (T-0) was measured immediately after applying the tape. Aged adhesion (T-24) was measured after 24 hours of continuous skin contact. Each sample was tested on six individuals with three replicates per individual for a total of 18 separate measurements. Reported values are averages of these eighteen measurements.

T-0 and T-24 values for various articles are found in Tables 1, 5–7, 10–22 and 24. Results in a particular table were performed with the same group of individuals under the same conditions. The values are reported in N/100 mm width.

Moisture Vapor Permeability

The moisture vapor permeability is measured according to ASTM E-96-80 using a modified Payne cup method. The method includes the following steps:

1. A 35 mm diameter sample of 1 mil (0.025 mm) thick material to be tested containing no perforations was cut.
2. The sample was entered between adhesive surfaces of two foil adhesive rings, each having a one inch (2.54) cm diameter hole. The holes of each ring were carefully aligned. Finger pressure was used to form a foil/sample/foil assembly that was flat, wrinkle-free, and had no void areas in the exposed sample.
3. A 4-ounce (0.14 kg) glass jar was filled half-way with distilled water. The jar was fitted with a screw-on cap having a 1.50 inch (3.8 cm) diameter hole in the center thereof and with a 1.75 inch (4.445 cm) diameter rubber washer having a 1.12 inch (2.84 cm) diameter hole in its center.
4. The rubber washer was placed on the lip of the jar and the foil/sample assembly was placed on the rubber washer. The lid was then screwed loosely on the jar.
5. The assembly was placed in a chamber at 100° F. (380° C.) and 20 percent relative humidity for four hours.
6. The cap was tightened inside the chamber so that the sample material was level with the cap (no bulging) and the rubber washer was in proper seating position.

7. The foil/sample assembly was removed from the chamber and weighed immediately to the nearest 0.01 grams (initial weight $W_1$).
8. The foil/sample assembly was returned to the chamber for at least 18 hours.
9. The foil/sample assembly was removed from the chamber and weighed immediately to the nearest 0.01 gram (final weight $W_2$).
10. The water vapor transmission in grams of water vapor transmitted per square meter of sample area in 24 hours was calculated according to the following formula:

$$MVT=(W_1-W_2)(4.74\times10^4)/T(\text{hours})$$

11. Three samples of each material were run, and the average was taken.

Moisture vapor permeability rates for various articles are reported in Table 1, 4, 5, and 7. The values are reported in $g/m^2/24$ hrs.

Keratin Assay

This assay was adapted from the assay disclosed in R. T. Tregear, P. Dirnhuber, The mass of keratin removed from the stratum corneum by stripping with adhesive tape, J. Invest. Dermatol. 38:375–381 (1961). The assay involved contacting the adhesive article after removal from the skin with an acidic dye solution, as described below. The dye binds to keratin protein within the mass of tissue removed from the skin. Following acid washings to remove excess dye, bound dye was released from the protein with a basic solution. The amount of dye released into the basic solution was correlated with a quantity of keratin by comparing a spectrophotometric measurement with a standard curve.

The standard curve was produced using aqueous solutions covering a range of concentrations of human keratin. These solutions were prepared by placing 5 ml, 10 ml, 20 ml, 40 ml, 80 ml or 150 ml of human keratin extract solution (7.7 mg/ml keratin, Sigma Chemical) into individual Centri/PorR™ (Spectrum Co.) centrifuge concentrators. A control was produced by placing 1 ml of water into a centrifuge concentrator. One ml of dye solution (0.5 g Chromotrope FB™ per liter of 0.01N $H_2SO_4$) was then added to each centrifuge concentrator. The keratin/dye mixture stood overnight at room temperature. Then, the tubes were centrifuged at 2000×g for 1 hour, after which the solution was decanted off.

Next, the centrifuge concentrators were washed by adding one ml of 0.1N $H_2SO_4$ to each centrifuge concentrator and shaking vigorously. The tubes were centrifuged again for 15 minutes, and the solution was decanted off to complete the washing step. The washing step was repeated 4 more times.

Following the last washing step, 3 mls of 0.25N NaOH was added to each centrifuge concentrator to form basic mixtures. The basic mixtures stood overnight at room temperature. Then, a portion of each solution was poured into a semi-micro cuvette, and an absorption measurement was made on a spectrophotometer at a wavelength of 508 nm. The standard curve was made with the values obtained from all of the solutions.

Two samples of known area were cut from each adhesive article to be analyzed. The samples were placed into separate 5 ml plastic tubes along with a control piece of adhesive article that had not been in contact with skin. Then, 4.5 mls of dye solution was added to each tube, and the tubes stood overnight at room temperature. Next, each tube was washed five times with 0.1N $H_2SO_4$. After the washings, 4.5 mls of 0.25N NaOH were added to each tube. The tubes stood overnight at room temperature to allow the release of all of the dye. A portion of each solution was poured in to a micro-cuvette, and the measurements was obtained as described with the standard solutions. The spectrophotometric measurements were corrected by subtracting the measurement from the control sample. The corrected measurements were compared to the standard curve to obtain quantities of keratin. Values were reported as mg of keratin per $cm^2$ of tape surface.

Keratin values obtained for various adhesive articles are reported in Table 23.

Aging Study

A portion of the adhesive article was tested for skin adhesion without any aging, as described above. Another portion of the same adhesive article was stored (aged) in a circulating-air oven at a temperature of 100° F. and at 60% relative humidity. Aged articles were tested for T-0 skin adhesion as described above either after 1 week or after 2 weeks of storage in the oven.

The results of the aging study performed on various articles are reported in Table 24.

Microsphere Preparation

Microsphere 1 (IOA:AA:EOA/97:2:1)

A monomer mixture was prepared by dissolving 4.8 g of acrylic acid (AA), 2.4 g of Carbowax™ 750 acrylate (polyethylene oxide acrylate) (EOA) and 1.13 g Lucidol™-70 (70% benzoyl peroxide) in 232.8 g of iso-octyl acrylate (IOA). A surfactant solution was prepared by dissolving 0.75 g of sodium dodecyl benzene sulfonate in 360 g of water. The monomer mixture then was added to the surfactant solution, and the resulting mixture was emulsified using a Gifford-Wood™ mixer until the droplet size was less than 1 μm. The emulsion was charged to a 1 liter baffled reactor, heated to 65° C., degassed with $N_2$ and allowed to react for 8 hours. Microspheres having an average diameter of about 2 μm were formed during the reaction period.

Microsphere 2 (IOA:NVP:AM90G/90:5:5)

The Microsphere 1 procedure was followed except that the monomer mixture was prepared by dissolving 12 g of N-vinyl pyrollidone (NVP), 12 g of AM90G (Shin-Nakamura "NK Ester"™ (polyethylene oxide acrylate)) and 1.13 Lucidol™-70 (70% benzoyl peroxide) in 216 g of iso-octyl acrylate (IOA). Microspheres having an average diameter of about 2 μm were formed during the reaction period.

Microsphere 3 (IOA:AA:EOA/97:2:1)

A monomer mixture was prepared by dissolving 4.8 g of acrylic acid (AA), 2.4 g of Carbowax™ 750 acrylate (polyethylene oxide acrylate) (EOA) and 1.13 g Lucidol™-70 (70% benzoyl peroxide) in 232.8 g of iso-octyl acrylate (IOA). A surfactant solution was prepared by dissolving 0.75 g of sodium dodecyl benzene sulfonate in 360 g of water. The monomer mixture then was added to the surfactant solution. The resulting mixture was charged to a 1 liter baffled reactor, stirred at 400 RPM, heated to 65° C., degassed with $N_2$ and allowed to react for 8 hours. Microspheres having an average diameter of about 60 μm were formed during the reaction period.

Microsphere 4 (IOA:AA:EOA/97:2:1)

The Microsphere 3 procedure was followed except that the stirring rate was 650 RPM. Microspheres having an average diameter of about 25 μm were formed during the reaction period.

Microsphere 5 (IOA:NVP:EOA/90:5:5)

The Microsphere 1 procedure was followed except that the monomer mixture was prepared by dissolving 12 g of N-vinyl pyrollidone (NVP), 12 g of Carbowax™ 750 acrylate (polyethylene oxide acrylate) (EOA) and 1.13 Lucidol™-70 (70% benzoyl peroxide) in 216 g of iso-octyl acrylate (IOA). Microspheres having an average diameter of about 2 μm were formed during the reaction period.

Microsphere 6 (IOA:AA:EOA/97:2:1)

The Microsphere 4 procedure was followed except that microspheres having an average diameter of about 23 μm were formed during the reaction period.

Microsphere 7 (IOA:AA:EOA/97:2:1)

The Microsphere 1 procedure was followed except that 0.19 g of $CBr_4$ were added to the monomer mixture. Microspheres having an average diameter of about 2 μm were formed during the reaction period.

Microsphere 8 (IOA:AA:BDA/95.5:2.5:2)

The Microsphere 3 procedure was followed except that the monomer mixture was prepared by dissolving 6 g of acrylic acid (AA), 4.8 g of Butanediol diacrylate (BDA) and 1.13 g Lucidol™-70 (70% benzoyl peroxide) in 229.2 g of iso-octyl acrylate (IOA). In addition, the stirring rate was 300 RPM. Microspheres having an average diameter of about 70 μm were formed during the reaction period.

Microsphere 9 (IOA:AmA/94:6)

The Microsphere 3 procedure was followed except that the monomer mixture was prepared by dissolving 14.4 g of Ammonium acrylate and 1.13 g Lucidol™-70 (70% benzoyl peroxide) in 225.6 g of iso-octyl acrylate (IOA). Microspheres, having an average diameter of about 41m, were formed during the reaction period.

Microsphere 10 (NEO-9:AA:HDDA/98:1:1)

The Microsphere 1 procedure was followed except that the monomer mixture was prepared by dissolving 2.4 g of acrylic acid (AA), 2.4 g of 1,6-hexanediol diacrylate (HDDA) and 1.13 Lucidol™-70 (70% benzoyl peroxide) in 235.2 g of vinyl neononanoate (Neo-9). Microspheres having an average diameter of about 2 μm were formed during the reaction period.

Microsphere 11 (IOA:AmA/98:2)

The Microsphere 1 procedure was followed except that the monomer mixture was prepared by dissolving 4.8 g of ammonium acrylate (AmA) and 1.13 g Lucidol™-70 (70% benzoyl peroxide) in 235.2 g of iso-octyl acrylate (IOA). Microspheres having an average diameter of about 2 μm were formed during the reaction period.

Microsphere 12 (IOA:AA/96:4)

The Microsphere 3 procedure was followed except that the monomer mixture was prepared by dissolving 4.8 g of acrylic acid (AA), and 1.13 g Lucidol™-70 (70% benzoyl peroxide) in 230.4 g of iso-octyl acrylate (IOA). Microspheres having an average diameter of about 60 μm were formed during the reaction period.

Microsphere 13 (IOA)

The Microsphere 3 procedure was followed except that the monomer mixture was prepared by dissolving 1.13 g Lucidol™-70 (70% benzoyl peroxide) in 240 g of iso-octyl acrylate (IOA). Microspheres having an average diameter of about 60 μm were formed during the reaction period. Microsphere 14 (IOA:AA:EOA/97:2:1)

The Microsphere 4 procedure was followed. Microspheres having an average diameter of 27 μm were formed during the reaction period.

Microsphere 15 (IOA:AA:EOA/97:2:1)

The Microsphere 4 procedure was followed except 0.10 g of $CBr_4$ was added to the monomer mixture to form a 0.04% $CBr_4$ solution. Microspheres having an average diameter of 23 μm were formed during the reaction period.

Microsphere 16 (IOA:AA:EOA/97:2:1) The Microsphere 4 procedure was followed except 0.19 g of $CBr_4$ was added to the monomer mixture to form a 0.08% $CBr_4$ solution. Microspheres having an average diameter of 22 μm were formed during the reaction period. Microsphere 17 (IOA:AA:EOA/97:2:1)

The Microsphere 4 procedure was followed except 0.48 g of $CBr_4$ was added to the monomer mixture to form a 0.20% $CBr_4$ solution. Microspheres having an average diameter of 30 μm were formed during the reaction period.

Matrix Preparation

Matrix Composition 1 (IOA/AA/EOA 70/15/15)

Matrix composition 1 was prepared following the procedures outlined in PCT US84/00506 and WO 84/03837 using a monomer mixture containing 70 parts by weight iso-octyl acrylate, 15 parts by weight acrylic acid, and 15 parts EOA.

Matrix Composition 2 (IOA/ACM 97/3)

This matrix composition was a copolymer of iso-octyl acrylate and acrylamide in a weight ratio of 97 to 3. The copolymer was prepared generally following the procedure outlined in U.S. Pat. No. 24,906. An ethyl acetate solution was prepared containing 37% monomers with an inherent viscosity of 1.2. The initiator was benzoyl peroxide (Lucidol™ 70 from Union Carbide, Danbury, Conn.).

Matrix Composition 3 (IOA/AA/PSM 96/2/2)

This matrix composition was prepared following the procedure outlined in U.S. Pat. No. 4,693,776. Specifically, the copolymerization reaction was performed in a sealed, one-quart amber bottle that had been purged by bubbling nitrogen through the solution at a flow rate of one liter per minute for two minutes before the bottle was sealed.

The solution purged by the nitrogen included 190 g iso-octyl acetate (IOA), 4 g acrylic acid (AA), 4 g 2-polystyrylethyl methacrylate macromer, 300 g ethyl acetate (A. R. grade), 0.6 g 2,2'-azobisiso-butyronitrile (commercially available from DuPont as VAZOR 64), and 2.5 g of a 1% solution of $CBr_4$ in iso-octyl acrylate which results in a $CBr_4$ charge of 0.012%. The sealed bottle was tumbled for 24 hours in a water bath at 55° C. to effect essentially complete polymerization. The resulting solution contained 38.65% copolymer comprised of 96% iso-octyl acrylate/2% acrylic acid/2% 2-polystyrylethyl methacrylate macromer. A dilute solution of this adhesive polymer in ethyl acetate had an inherent viscosity of 0.904 dl/g. The Brookfield viscosity measurement was 6,000 centipoise.

Matrix Composition 4 (IOA/VOAc/AA/HDDA 89/6/6/2/0.1)

This matrix composition was prepared generally according to the procedure outlined in Example 11 of published patent application EP 0 554 832 A1.

Article Preparation

Adhesive blends were prepared by mixing an aqueous dispersion of microspheres with the appropriate matrix polymer either in solution or as a latex. Mixing was effected overnight by rolling on a ball mill or by stirring with an air-driven stirrer at 200–300 rpm for 10–60 minutes.

For adhesive testing, adhesive blends were coated onto a silicone-coated release paper using a knife-over-bed coater, with the knife orifice set to deliver the specified dry weight of adhesive. The layer was dried in a circulating-air oven at 220° F. for 10–20 minutes. The backing was laminated to the adhesive by bringing the layers into contact between rolls of a laminator. For sheer-creep compliance testing, adhesive blends were coated directly onto the backing, air dried for 30 minutes, and oven dried at 220° F. for 10–20 minutes.

The following articles were prepared. Reported coat thicknesses have an uncertainty of about ±5%.

Article 1

Article 1 featured a blend of microspheres 2 and matrix 1 (20 phr microspheres) coated onto a polyurethane blown microfiber backing. The coating thickness of adhesive blend was approximately 50 μm.

Article 2

Article 2 featured a blend of microspheres 2 and matrix 1 (30 phr microspheres) coated onto a polyurethenae blown microfiber backing. The coating thickness of adhesive blend was approximately 50 μm.

Article 3

Article 3 featured a blend of microspheres 2 and matrix 1 (40 phr microspheres) coated onto a polyurethenae blown microfiber backing. The coating thickness of adhesive blend was approximately 50 μm.

Article 4

Article 4 featured a blend of microspheres 2 and matrix 1 (20 phr microspheres) coated onto a polyester backing. The coating thickness of adhesive blend was approximately 150 μm.

Article 5

Article 5 featured a blend of microspheres 2 and matrix 1 (30 phr microspheres) coated onto a polyester backing. The coating thickness of adhesive blend was approximately 150 μm.

Article 6

Article 6 featured a blend of microspheres 2 and matrix 1 (40 phr microspheres) coated onto a polyester backing. The coating thickness of adhesive blend was approximately 150 μm.

Article 7

Article 7 featured a blend of microspheres 6 and matrix 1 (20 phr microspheres) coated onto a polyester backing. The coating thickness of adhesive blend was approximately 150 μm. Equilibrium creep compliance tests were performed.

Article 8

Article 8 featured a blend of microspheres 6 and matrix 1 (40 phr microspheres) coated onto a polyester backing. The coating thickness of adhesive blend was approximately 150 μm. Equilibrium creep compliance tests were performed.

Article 9

Article 9 featured a blend of microspheres 3 and matrix 1 (20 phr microspheres) coated onto a polyurethane blown microfiber backing. The coating thickness of adhesive blend was approximately 50 μm. Equilibrium creep compliance tests were performed with the same adhesive on a polyester backing.

Article 10

Article 10 featured a blend of microspheres 3 and matrix 1 (40 phr microspheres) coated onto a polyurethane blown microfiber backing. The coating thickness of adhesive blend was approximately 50 μm. Equilibrium creep compliance tests were performed with the same adhesive on a polyester backing.

Article 11

Article 11 featured a blend of microspheres 4 and matrix 1 (20 phr microspheres) coated onto a polyurethane blown microfiber backing. The coating thickness of adhesive blend was approximately 50 μm. Equilibrium creep compliance tests were performed with the same adhesive on a polyester backing.

Article 12

Article 12 featured a blend of microspheres 4 and matrix 1 (40 phr microspheres) coated onto a polyurethane blown microfiber backing. The coating thickness of adhesive blend was approximately 50 μm. Equilibrium creep compliance tests were performed with the same adhesive on a polyester backing.

Article 13

Article 13 featured a blend of microspheres 1 and matrix 1 (20 phr microspheres) coated onto a polyurethane blown microfiber backing. The coating thickness of adhesive blend was approximately 50 μm.

Article 14

Article 14 featured a blend of microspheres 1 and matrix 1 (40 phr microspheres) coated onto a polyurethane blown microfiber backing. The coating thickness of adhesive blend was approximately 50 μm.

Article 15

Article 15 featured a blend of microspheres 5 and matrix 1 (20 phr microspheres) coated onto a polyurethane blown microfiber backing. The coating thickness of adhesive blend was approximately 50 μm.

Article 16

Article 16 featured a blend of microspheres 5 and matrix 1 (40 phr microspheres) coated onto a polyurethane blown microfiber backing. The coating thickness of adhesive blend was approximately 50 μm.

Article 17

Article 17 featured a blend of microspheres 3 and matrix 1 (20 phr microspheres) coated onto a polyurethane blown microfiber backing. The coating thickness of adhesive blend was approximately 50 μm.

Article 18

Article 18 featured a blend of microspheres 3 and matrix 1 (40 phr microspheres) coated onto a polyurethane blown microfiber backing. The coating thickness of adhesive blend was approximately 50 μm.

Article 19

Article 19 featured a blend of microspheres 4 and matrix 1 (20 phr microspheres) coated onto a polyurethane blown microfiber backing. The coating thickness of adhesive blend was approximately 50 μm.

Article 20

Article 20 featured a blend of microspheres 4 and matrix 1 (40 phr microspheres) coated onto a polyurethane blown microfiber backing. The coating thickness of adhesive blend was approximately 50 μm.

Article 21

Article 21 featured a blend of microspheres 6 and matrix 1 (20 phr microspheres) coated onto a polyurethane blown microfiber backing. The coating thickness of adhesive blend was approximately 50 µm.

Article 22

Article 22 featured a blend of microspheres 6 and matrix 1 (40 phr microspheres) coated onto a polyurethane blown microfiber backing. The coating thickness of adhesive blend was approximately 50 µm.

Article 23

Article 23 featured a blend of microspheres 3 and matrix 1 (20 phr microspheres) coated onto a polyurethane blown microfiber backing. The coating thickness of adhesive blend was approximately 50 µm.

Article 24

Article 24 featured a blend of microspheres 3 and matrix 1 (40 phr microspheres) coated onto a polyurethane blown microfiber backing. The coating thickness of adhesive blend was approximately 50 µm.

Article 25

Article 25 featured a blend of microspheres 4 and matrix 1 (20 phr microspheres) coated onto a polyurethane blown microfiber backing. The coating thickness of adhesive blend was approximately 50 µm.

Article 26

Article 26 featured a blend of microspheres 4 and matrix 1 (40 phr microspheres) coated onto a polyurethane blown microfiber backing. The coating thickness of adhesive blend was approximately 50 µm.

Article 27

Article 27 featured a blend of microspheres 5 and matrix 1 (30 phr microspheres) coated onto a polyester backing. The coating thickness of adhesive blend was approximately 150 µm.

Article 28

Article 28 featured a blend of microspheres 5 and matrix 1 (40 phr microspheres) coated onto a polyester backing. The coating thickness of adhesive blend was approximately 150 µm.

Article 29

Article 29 featured a blend of microspheres 5 and matrix 1 (50 phr microspheres) coated onto a polyester backing. The coating thickness of adhesive blend was approximately 50 µm.

Article 30

Article 30 featured a blend of microspheres 7 and matrix 1 (20 phr microspheres) coated onto a polyester backing. The coating thickness of adhesive blend was approximately 150 µm. Equilibrium creep compliance tests were performed.

Article 31

Article 31 featured a blend of microspheres 7 and matrix 1 (30 phr microspheres) coated onto a polyester backing. The coating thickness of adhesive blend was approximately 150 µm. Equilibrium creep compliance tests were performed.

Article 32

Article 32 featured a blend of microspheres 7 and matrix 1 (40 phr microspheres) coated onto a polyester backing. The coating thickness of adhesive blend was approximately 150 µm. Equilibrium creep compliance tests were performed.

Article 33

Article 33 featured a blend of microspheres 7 and matrix 1 (50 phr microspheres) coated onto a polyester backing. The coating thickness of adhesive blend was approximately 150 µm. Equilibrium creep compliance tests were performed.

Article 34

Article 34 featured a blend of microspheres 7 and matrix 1 (20 phr microspheres) coated onto a polyester backing. The coating thickness of adhesive blend was approximately 150 µm. The article was treated with sterilizing gamma radiation. Equilibrium creep compliance tests were performed.

Article 35

Article 35 featured a blend of microspheres 7 and matrix 1 (30 phr microspheres) coated onto a polyester backing. The coating thickness of adhesive blend was approximately 150 µm. The article was treated with sterilizing gamma radiation. Equilibrium creep compliance tests were performed.

Article 36

Article 36 featured a blend of microspheres 7 and matrix 1 (40 phr microspheres) coated onto a polyester backing. The coating thickness of adhesive blend was approximately 150 µm. The article was treated with sterilizing gamma radiation. Equilibrium creep compliance tests were performed.

Article 37

Article 37 featured a blend of microspheres 7 and matrix 1 (50 phr microspheres) coated onto a polyester backing. The coating thickness of adhesive blend was approximately 150 µm. The article was treated with sterilizing gamma radiation. Equilibrium creep compliance tests were performed.

Article 38

Article 38 featured a blend of microspheres 7 and matrix 1 (20 phr microspheres) coated onto a polyurethane blown microfiber backing. The coating thickness of adhesive blend was approximately 50 µm.

Article 39

Article 39 featured a blend of microspheres 7 and matrix 1 (30 phr microspheres) coated onto a polyurethane blown microfiber backing. The coating thickness of adhesive blend was approximately 50 µm.

Article 40

Article 40 featured a blend of microspheres 7 and matrix 1 (40 phr microspheres) coated onto a polyurethane blown microfiber backing. The coating thickness of adhesive blend was approximately 50 µm.

Article 41

Article 41 featured a blend of microspheres 7 and matrix 1 (50 phr microspheres) coated onto a polyurethane blown microfiber backing. The coating thickness of adhesive blend was approximately 50 μm.

Article 42

Article 42 featured a blend of microspheres 1 and matrix 1 (20 phr microspheres) coated onto a polyurethane blown microfiber backing. The coating thickness of adhesive blend approximately 50 μm.

Article 43

Article 43 featured a blend of microspheres 1 and matrix 1 (40 phr microspheres) coated onto a polyurethane blown microfiber backing. The coating thickness of adhesive blend was approximately 50 μm.

Article 44

Article 44 featured a blend of microspheres 8 and matrix 1 (20 phr microspheres) coated onto a Morthane™ PE-44-203 backing (polyurethane film with a thickness of 27 μm) from Morton International. The coating thickness of adhesive blend was approximately 25 μm. Equilibrium creep compliance tests were performed with the same adhesive on a polyester backing.

Article 45

Article 45 featured a blend of microspheres 8 and matrix 1 (40 phr microspheres) coated onto a Morthane™ PE-44-203 backing. The coating thickness of adhesive blend was approximately 25 μm. Articles were treated with sterilizing gamma radiation. Equilibrium creep compliance tests were performed with the same adhesive on a polyester backing.

Article 46

Article 46 featured a blend of microspheres 9 and matrix 1 (20 phr microspheres) coated onto a Morthane™ PE-44-203 backing. The coating thickness of adhesive blend was approximately 25 μm. Equilibrium creep compliance tests were performed with the same adhesive on a polyester backing.

Article 47

Article 47 featured a blend of microspheres 9 and matrix 1 (40 phr microspheres) coated onto a Morthane™ PE-44-203 backing. The coating thickness of adhesive blend was approximately 25 μm. Equilibrium creep compliance tests were performed with the same adhesive on a polyester backing.

Article 48

Article 48 featured a blend of microspheres 10 and matrix 1 (20 phr microspheres) coated onto a Morthane™ PE-44-203 backing. The coating thickness of adhesive blend was approximately 25 μm. Equilibrium creep compliance tests were performed with the same adhesive on a polyester backing.

Article 49

Article 49 featured a blend of microspheres 10 and matrix 1 (40 phr microspheres) coated onto a Morthane™ PE-44-203 backing. The coating thickness of adhesive blend was approximately 25 μm. Equilibrium creep compliance tests were performed with the same adhesive on a polyester backing.

Article 50

Article 50 featured a blend of microspheres 11 and matrix 1 (20 phr microspheres) coated onto a Morthane™ PE-44-203 backing. The coating thickness of adhesive blend was approximately 25 μm. Equilibrium creep compliance tests were performed with the same adhesive on a polyester backing.

Article 51

Article 51 featured a blend of microspheres 11 and matrix 1 (40 phr microspheres) coated onto a Morthane™ PE-44-203 backing. The coating thickness of adhesive blend was approximately 25 μm. Equilibrium creep compliance tests were performed with the same adhesive on a polyester backing.

Article 52

Article 52 featured a blend of microspheres 1 and matrix 4 (33 phr microspheres) coated onto a Morthane™ PE-44-203 backing. The coating thickness of adhesive blend was approximately 25 μm. Equilibrium creep compliance tests were performed with the same adhesive on a polyester backing.

Article 53

Article 53 featured a blend of microspheres 1 and matrix 4 (100 phr microspheres) coated onto a Morthane™ PE-44-203 backing. The coating thickness of adhesive blend was approximately 25 μm. Equilibrium creep compliance tests were performed with the same adhesive on a polyester backing.

Article 54

Article 54 featured a blend of microspheres 1 and matrix 4 (300 phr microspheres) coated onto a Morthane™ PE-44-203 backing. The coating thickness of adhesive blend was approximately 25 μm. Equilibrium creep compliance tests were performed with the same adhesive on a polyester backing.

Article 55

Article 55 featured a blend of microspheres 5 and matrix 1 (30 phr microspheres) coated onto a Morthane™ PE-44-203 backing. The coating thickness of adhesive blend was approximately 25 μm.

Article 56

Article 56 featured a blend of microspheres 12 and matrix 2 (25 phr microspheres) coated onto a Morthane™ PE-44-203 backing. The coating thickness of adhesive blend was approximately 25 μm.

Article 57

Article 57 featured a blend of microspheres 12 and matrix 3 (25 phr microspheres) coated onto a Morthane™ PE-44-203 backing. The coating thickness of adhesive blend approximately 25 μm.

Article 58

Article 58 featured a blend of microspheres 13 and matrix 2 (25 phr microspheres) coated onto a Morthane™ PE-44-

203 backing. The coating thickness of adhesive blend was approximately 25 μm.

Article 59

Article 59 featured a blend of microspheres 1 and matrix 4 (33 phr microspheres) coated onto a Morthane™ PE-44-203 backing. The coating thickness of adhesive blend was approximately 20 μm.

Article 60

Article 60 featured a blend of microspheres 1 and matrix 4 (100 phr microspheres) coated onto a Morthane™ PE-44-203 backing. The coating thickness of adhesive blend was approximately 20 μm.

Article 61

Article 61 featured a blend of microspheres 1 and matrix 4 (300 phr microspheres) coated onto a Morthane™ PE-44-203 backing. The coating thickness of adhesive blend was approximately 20 μm.

Article 62

Article 62 featured a blend of microspheres 3 and matrix 4 (33 phr microspheres) coated onto a Morthane™ PE-44-203 backing. The coating thickness of adhesive blend was approximately 29 μm. Equilibrium creep compliance tests were performed with the same adhesive on a polyester backing.

Article 63

Article 63 featured a blend of microspheres 3 and matrix 4 (100 phr microspheres) coated onto a Morthane™ PE-44-203 backing. The coating thickness of adhesive blend was approximately 29 μm. Equilibrium creep compliance tests were performed with the same adhesive on a polyester backing.

Article 64

Article 64 featured a blend of microspheres 3 and matrix 4 (300 phr microspheres) coated onto a Morthane™ PE-44-203 backing. The coating thickness of adhesive blend was approximately 29 μm. Equilibrium creep compliance tests were performed with the same adhesive on a polyester backing.

Article 65

Article 65 featured a blend of microspheres 3 and matrix 4 (33 phr microspheres) coated onto a Morthane™ PE-44-203 backing. The coating thickness of adhesive blend was approximately 25 μm.

Article 66

Article 66 featured a blend of microspheres 3 and matrix 4 (100 phr microspheres) coated onto a Morthane™ PE-44-203 backing. The coating thickness of adhesive blend was approximately 25 μm.

Article 67

Article 67 featured a blend of microspheres 1 and matrix 4 (33 phr microspheres) coated onto a Morthane™ PE-44-203 backing. The coating thickness of adhesive blend was approximately 62 μm.

Article 68

Article 68 featured a blend of microspheres 1 and matrix 4 (100 phr microspheres) coated onto a Morthane™ PE-44-203 backing. The coating thickness of adhesive blend was approximately 62 μm.

Article 69

Article 69 featured a blend of microspheres 1 and matrix 4 (300 phr microspheres) coated onto a Morthane™ PE-44-203 backing. The coating thickness of adhesive blend was approximately 62 μm.

Article 70

Article 70 featured a blend of microspheres 3 and matrix 4 (33 phr microspheres) coated onto a Morthane™ PE-44-203 backing. The coating thickness of adhesive blend was approximately 62 μm.

Article 71

Article 71 featured a blend of microspheres 3 and matrix 4 (100 phr microspheres) coated onto a Morthane™ PE-44-203 backing. The coating thickness of adhesive blend was approximately 62 μm.

Article 72

Article 72 featured a blend of microspheres 3 and matrix 4 (300 phr microspheres) coated onto a Morthane™ PE-44-203 backing. The coating thickness of adhesive blend was approximately 62 μm.

Article 73

Article 73 featured a blend of microspheres 14 and matrix 14 (30 phr microspheres) coated onto a polyurethane blown microfiber backing. The coating thickness of adhesive blend was approximately 50 μm.

Article 74

Article 74 featured a blend of microspheres 15 and matrix 1 (30 phr microspheres) coated onto a polyurethane blown microfiber backing. The coating thickness of adhesive blend was approximately 50 μm.

Article 75

Article 75 featured a blend of microspheres 16 and matrix 1 (30 phr microspheres) coated onto a polyurethane blown microfiber backing. The coating thickness of adhesive blend was approximately 50 μm.

Article 76

Article 76 featured a blend of microspheres 17 and matrix 1 (30 phr microspheres) coated onto a polyurethane blown microfiber backing. The coating thickness of adhesive blends was approximately 50 μm.

Article 77

Article 77 featured a blend of microspheres 1 and matrix 1 (20 phr microspheres) coated onto a polyurethane blown microfiber backing. The coating thickness of adhesive blend was approximately 50 μm.

Article 78

Article 78 featured a blend of microspheres 1 and matrix 1 (40 phr microspheres) coated onto a polyurethane blown microfiber backing. The coating thickness of adhesive blend was approximately 50 μm.

Article 79

Article 79 featured a blend of microspheres 5 and matrix 1 (20 phr microspheres) coated onto a polyurethane blown microfiber backing. The coating thickness of adhesive blend was approximately 50 µm.

Article 80

Article 80 featured a blend of microspheres 5 and matrix 1 (40 phr microspheres) coated onto a polyurethane blown microfiber backing. The coating thickness of adhesive blend was approximately 50 µm.

Article 81

Article 81 featured a blend of microspheres 1 and atrix 1 (30 phr microspheres) coated onto a polyurethane backing (Estane 58237, commercially available from B. F. Goodrich & Co.). The coating thickness of adhesive blend was approximately 25 µm. Article 81 had an inverted buffered saline moisture vapor transmission rate value of 16,000 g/m$^2$/24 hrs. (measured according to the procedure described in co-pending, commonly assigned U.S. patent application Ser. No. 08/726510 in the name of Heinecke et al. entitled "Moisture-Regulating Adhesive Dressing," hereby incorporated by reference) and an inverted water moisture vapor transmission rate value of 1540 g/m$^2$/24 hrs., as measured according to ASTM E-96-80.

Comparative Article 1

Comparative article 1 featured polymer matrix 1 coated onto a polyester backing. The coating thickness of polymer matrix was approximately 150 µm. Equilibrium creep compliance tests were performed.

Comparative Article 2

Comparative article 2 was Comfort Strip™, commercially available from Minnesota Mining and Manufacturing Co., Saint Paul, Minn.

Comparative Article 3

Comparative article 3 was Comfort Strip™, commercially available from Minnesota Mining and Manufacturing Co., Saint Paul, Minn.

Comparative Article 4

Comparative article 4 was Tegaderm HPTM, commercially available from Minnesota Mining and Manufacturing Co., Saint Paul, Minn.

Comparative Article 5

Comparative article 5 featured microspheres 7 coated onto a polyester backing. The coating thickness of microspheres was approximately 150 µm. Equilibrium creep compliance tests were performed.

Comparative Article 6

Comparative article 6 featured microspheres 7 coated onto a polyester backing. The coating thickness of microspheres was approximately 150 µm. The article is treated with sterilizing gamma radiation. Equilibrium creep compliance tests were performed.

Comparative Article 7

Comparative article 7 was Tegaderm™, commercially available from Minnesota Mining and Manufacturing Co., Saint Paul, Minn.

Comparative Article 8

Comparative article 8 was Tegaderm™, commercially available from Minnesota Mining and Manufacturing Co., Saint Paul, Minn.

Comparative Article 9

Comparative article 9 was Tegaderm HP™, commercially available from Minnesota Mining and Manufacturing Co., Saint Paul, Minn.

Comparative Article 10

Comparative article 10 was Tegaderm HP™, commercially available from Minnesota Mining and Manufacturing Co., Saint Paul, Minn.

Comparative Article 11

Comparative article 11 featured microspheres 1 coated onto a Morthane™ PE-44-203 backing from Morton International. The coating thickness of microspheres was approximately 25 µm.

Comparative Article 12

Comparative article 12 featured matrix 4 coated onto a Morthane™ PE-44-203 backing. The coating thickness of matrix was approximately 20 µm.

Comparative Article 13

Comparative article 13 was Tegaderm™, commercially available from Minnesota Mining and Manufacturing Co., Saint Paul, Minn.

Comparative Article 14

Comparative article 14 featured matrix 4 coated onto a Morthane™ PE-44-203 backing. The coating thickness of matrix was approximately 29 µm.

Comparative Article 15

Comparative article 15 featured microspheres 3 coated onto a Morthane™ PE-44-203 backing. The coating thickness of microspheres was approximately 29 µm.

Comparative Article 16

Comparative article 16 was Tegaderm™, commercially available from Minnesota Mining and Manufacturing Co., Saint Paul, Minn.

Comparative Article 17

Comparative article 17 was Tegaderm™, commercially available from Minnesota Mining and Manufacturing Co., Saint Paul, Minn.

Comparative Article 18

Comparative article 18 featured microspheres 1 coated onto a Morthane™ PE-44-203 backing. The coating thickness of microspheres was approximately 62 µm.

Comparative Article 19

Comparative article 19 featured matrix 4 coated onto a Morthane™ PE-44-203 backing. The coating thickness of matrix was approximately 62 µm.

Comparative Article 20

Comparative article 20 was Tegaderm™, commercially available from Minnesota Mining and Manufacturing Co., Saint Paul, Minn.

Comparative Article 21

Comparative article 20 featured matrix 1 coated onto a polyurethane blown microfiber backing. The coating thickness of matrix was approximately 50 μm.

Comparative Article 22

Comparative article 22 was Comfort Strip™, commercially available from Minnesota Mining and Manufacturing Co., Saint Paul, Minn.

TABLE 1

| Article | T-0 | T-24 | MVTR |
|---|---|---|---|
| 1 | 1.51 | 6.45 | 666 |
| 2 | 1.08 | 5.02 | 999 |
| 3 | 1.04 | 5.25 | 947 |

TABLE 2

| Article | Compliance |
|---|---|
| 4 | 1.87 |
| 5 | 1.86 |
| 6 | 1.74 |

TABLE 3

| Article | Compliance |
|---|---|
| C1 | 2.46 |
| 7 | 1.73 |
| 8 | 1.42 |

TABLE 4

| Article | MVTR | Compliance |
|---|---|---|
| 9 | 690 | 1.93 |
| 10 | 698 | 1.81 |
| 11 | 640 | 1.92 |
| 12 | 665 | 1.66 |

TABLE 5

| Article | T-0 | T-24 | MVTR |
|---|---|---|---|
| 13 | 2.51 | 9.50 | 652 |
| 14 | 2.36 | 9.07 | 520 |
| 15 | 1.70 | 8.22 | 566 |
| 16 | 1.54 | 6.64 | 711 |
| C2 | 3.44 | 9.42 | |

TABLE 6

| Article | T-0 | T-24 |
|---|---|---|
| 17 | 1.16 | 7.30 |
| 18 | 1.24 | 7.26 |
| 19 | 1.16 | 6.87 |
| 20 | 1.39 | 8.26 |
| C3 | 3.09 | 8.19 |

TABLE 7

| Article | T-0 | T-24 | MVTR |
|---|---|---|---|
| 21 | 1.39 | 6.02 | 1238 |
| 22 | 1.66 | 6.60 | 849 |
| 23 | 1.66 | 5.56 | 1113 |
| 24 | 1.62 | 4.83 | |
| 25 | 1.70 | 4.79 | 1001 |
| 26 | 1.58 | 4.48 | 961 |
| C4 | 1.43 | 3.05 | 1126 |

TABLE 8

| Article | Compliance |
|---|---|
| 27 | 1.05 |
| 28 | 1.06 |
| 29 | 0.97 |

TABLE 9

| Article | Compliance |
|---|---|
| C5 | 3.81 |
| 30 | 3.07 |
| 31 | 3.16 |
| 32 | 3.05 |
| 33 | 3.13 |
| C6 | 1.07 |
| 34 | 1.68 |
| 35 | 1.59 |
| 36 | 1.52 |
| 37 | 1.41 |

TABLE 10

| Article | T-0 | T-24 |
|---|---|---|
| 38 | 2.78 | 6.99 |
| 39 | 3.09 | 8.69 |
| 40 | 3.17 | 8.88 |
| 41 | 2.82 | 7.07 |
| C7 | 3.09 | 5.40 |
| 42 | 1.04 | 6.49 |
| 43 | 1.20 | 9.61 |
| C8 | 1.74 | 5.17 |

TABLE 11

| Article | T-0 | T-24 | Compliance |
|---|---|---|---|
| 44 | 0.54 | 1.70 | 1.70 |
| 45 | 0.97 | 0.93 | 1.67 |
| 46 | 1.04 | 4.13 | 1.99 |
| 47 | 0.97 | 4.02 | 1.89 |

TABLE 12

| Article | T-0 | T-24 | Compliance |
|---|---|---|---|
| 48 | 0.77 | 3.90 | 1.74 |
| 49 | 0.54 | 3.24 | 1.12 |

TABLE 13

| Article | T-0 | T-24 | Compliance |
| --- | --- | --- | --- |
| 50 | 1.35 | 5.37 | 2.37 |
| 51 | 1.27 | 5.60 | 1.79 |

TABLE 14

| Article | T-0 | T-24 | Compliance |
| --- | --- | --- | --- |
| C9 | 0.97 | 1.31 | 0.65 |
| 52 | 1.54 | 3.82 | 1.20 |
| 53 | 1.35 | 3.47 | 1.02 |
| 54 | 1.16 | 2.51 | 0.86 |
| 55 | 5.71 | 8.61 | |

TABLE 15

| Article | T-0 | T-24 |
| --- | --- | --- |
| 56 | 2.74 | 4.90 |
| 57 | 2.59 | 6.18 |

TABLE 16

| Article | T-0 | T-24 |
| --- | --- | --- |
| 58 | 2.43 | 6.49 |
| C10 | 1.47 | 3.82 |

TABLE 17

| Article | T-0 | T-24 |
| --- | --- | --- |
| C11 | 1.39 | 1.97 |
| 59 | 2.16 | 3.59 |
| 60 | 1.89 | 2.86 |
| 61 | 1.54 | 2.12 |
| C12 | 2.47 | 3.71 |
| C13 | 2.39 | 5.91 |

TABLE 18

| Article | T-0 | T-24 | Compliance |
| --- | --- | --- | --- |
| C14 | 1.85 | 4.29 | 1.31 |
| C15 | 0.69 | 1.85 | 0.47 |
| 62 | 1.66 | 3.98 | 1.23 |
| 63 | 1.93 | 3.28 | 0.93 |
| 64 | | | 0.80 |
| C16 | 2.39 | 5.91 | |

TABLE 19

| Article | T-0 | T-24 |
| --- | --- | --- |
| 65 | 2.24 | 3.59 |
| 66 | 2.57 | 3.86 |
| C17 | 2.32 | 4.98 |

TABLE 20

| Article | T-0 | T-24 |
| --- | --- | --- |
| C18 | 2.28 | 4.13 |
| 67 | 3.71 | 7.37 |
| 68 | 3.09 | 6.45 |
| 69 | 2.05 | 4.36 |
| C19 | 4.17 | 6.87 |

TABLE 21

| Article | T-0 | T-24 |
| --- | --- | --- |
| 70 | 3.5 | 7.41 |
| 71 | 3.17 | 4.59 |
| 72 | 2.43 | 4.56 |
| C20 | 1.81 | 4.44 |

TABLE 22

| Article | T-0 | T-24 |
| --- | --- | --- |
| 73 | 1.51 | 5.83 |
| 74 | 1.43 | 6.02 |
| 75 | 1.54 | 5.71 |
| 76 | 1.70 | 5.79 |
| C21 | 1.16 | 4.56 |

TABLE 23

| Article | Avg. Keratin $\mu g/cm^2$ |
| --- | --- |
| 73 | 109 |
| 74 | 101 |
| 75 | 92 |
| 76 | 214 |
| C21 | 129 |

TABLE 24

Aging Study

| Article | T-0 | Age |
| --- | --- | --- |
| 77 | 2.12 | Age 0 |
| 78 | 1.97 | " |
| 79 | 1.43 | " |
| 80 | 1.31 | " |
| C22 | 2.90 | " |
| 77 | 1.89 | 1 week |
| 78 | 1.97 | " |
| 79 | 1.47 | " |
| 80 | 1.43 | " |
| C22 | 2.90 | " |
| 77 | 2.28 | 2 week |
| 78 | 2.28 | " |
| 79 | 1.70 | " |
| 80 | 1.47 | " |
| C22 | 2.90 | " |

What is claimed is:

1. An article adapted for adhesion to the skin of a patient comprising a substrate having a surface at least a portion of which is provided with a pressure sensitive adhesive composition comprising a blend of (a) discrete, tacky, crosslinked polymer microspheres that comprise a polymer comprising the reaction product of at least one free radically polymerizable monomer, and (b) a polymer matrix, said adhesive composition having a substantially smooth, exposed surface available for adhesion.

2. The article of claim 1, wherein said article is in the form of a skin patch.

3. The article of claim 1, wherein said article is in the form of a wound dressing.

4. The article of claim 1, wherein said article is in the form of an adhesive bandage.

5. The article of claim 1, wherein said article is in the form of an island dressing.

6. The article of claim 1, wherein the thickness of said adhesive composition on said substrate is between about 10 micrometers and about 300 micrometers.

7. The article of claim 1, wherein said article is substantially transparent upon observation by the naked eye.

8. The article of claim 1, wherein said adhesive composition is in the form of substantially continuous, coating on said surface of said substrate.

9. The article of claim 1, wherein said adhesive composition is in the form of a discontinuous coating on said surface of said substrate.

* * * * *

UNITED STATES PATENT AND TRADEMARK OFFICE
CERTIFICATE OF CORRECTION

PATENT NO. : 6,479,073 B1
DATED : November 12, 2002
INVENTOR(S) : Donald H. Lucast and Richard J. Goetz It is certified that error appears in the above-identified patent and that said Letters Patent is hereby corrected as shown below:

Column 9,
Line 22, after "about" insert -- 5%. -- and start a new paragraph with "Use".

Column 11,
Line 59, delete "cm2" and insert in place thereof -- $cm^2$ --.

Column 12,
Line 63, delete "(380º" and insert in place thereof -- (38º --.

Column 15,
Line 27, delete "41m," and insert in place thereof -- 41 $\mu$m, --.
Line 56, "Micro-" should start a new paragraph.

Column 16,
Line 3, "Microsphere 17" should start a new paragraph.
Line 33, delete "VAZOR" and insert in place thereof -- $VAZO^R$ --.

Column 17,
Lines 6 and 12, delete "polyurethenae" and insert in place thereof -- polyurethane --.

Column 25,
Line 15, delete "atrix" and insert in place thereof -- matrix --.
Line 47, delete "HPTM" insert in place thereof -- $HP^{TM}$ --.

Column 32,
Line 4, delete "continuous," and insert in place thereof -- continuous --.

Signed and Sealed this

Fourth Day of January, 2005

JON W. DUDAS
*Director of the United States Patent and Trademark Office*